United States Patent [19]

Strom

[11] 4,361,708
[45] Nov. 30, 1982

[54] FORMATION OF BIPHENOLS

[75] Inventor: Robert M. Strom, Midland, Mich.

[73] Assignee: The Dow Chemical Company, Midland, Mich.

[21] Appl. No.: 241,343

[22] Filed: Mar. 6, 1981

[51] Int. Cl.$^3$ ............................................. C07C 39/12
[52] U.S. Cl. .................................... 568/730; 568/717; 568/722
[58] Field of Search ................ 568/730, 722, 723, 717

[56] References Cited

U.S. PATENT DOCUMENTS 3,555,052  1/1971  Yonemitsu et al. ................. 568/730
3,804,865  4/1974  Rutledge ............................ 568/730
4,180,686 12/1979  Dodd .................................. 568/730
4,195,189  3/1980  Earley ................................ 568/730

OTHER PUBLICATIONS

Blanchard "J. Organic Chem." vol. 25 (1960) pp. 264–266.
Attree et al. "J. Chem. Soc." (1931) pp. 144–173.

Primary Examiner—Werren B. Lone
Attorney, Agent, or Firm—Douglas N. Deline

[57] ABSTRACT

Substituted biphenols are produced by heating substituted phenols in nitrobenzene solvent in the presence of a heterogeneous oxidative coupling catalyst without the addition of oxygen-containing gas.

9 Claims, No Drawings

FORMATION OF BIPHENOLS

BACKGROUND OF THE INVENTION

The invention relates to an improved method of producing binary self condensation products of phenols. The products formed are substituted biphenols and are preferably 2,2',6,6'-tetrahydrocarbyl-p,p'-biphenols. According to an additional object of the invention, the tertiary alkyl-substituted biphenols may be easily dealkylated to yield the corresponding dealkylated biphenol product.

The biphenols are useful antioxidants and stabilizers in a variety of organic substances. The biphenols are also useful as components of polyester resins, for example, in the reaction with dicarboxylic acids such as terephthalic acid.

U.S. Pat. No. 3,555,052, published Jan. 12, 1971, disclosed that reduced noble metals were suitable catalysts for the oxidative coupling of phenols in the presence of oxygen to form diphenoquinones or polyarylene ethers. At column 4, line 44, it was stated that a suitable solvent for the reaction was nitrobenzene.

Prior art processes have employed oxygen or an oxygen-containing gas in order to effect the oxidative coupling reaction or alternatively an equivalent amount of a metal oxide such as silver oxide or copper oxide. These latter methods are disclosed in Blanchard, *J. Org. Chem.*, 25, 264 (1960) and U.S. Pat. No. 4,195,189, respectively.

SUMMARY OF THE INVENTION

The present invention comprises an improved process for the oxidative coupling of phenols. Accordingly, biphenol carbon-carbon reaction products are formed in accordance with the following general reactions depending on the reactive sites available in the phenol employed.

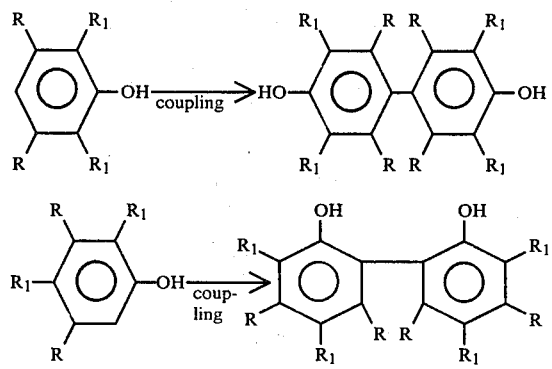

Each R is either hydrogen, halogen, or $R_1$; and each $R_1$ is a substituent having up to 10 carbons selected from hydrocarbon, halohydrocarbon or hydrocarbonoxy. Preferred phenol reactants are 2,6-disubstituted phenols which couple to form 2,2',6,6'-tetra-substituted-p,p'-biphenol. Most preferred are 2,6-dialkyl-substituted phenols.

According to the invention, the above-described substituted phenols are contacted in nitrobenzene solvent in the presence of a heterogeneous oxidative coupling catalyst without the presence of additional amounts of oxygen or an oxygen-containing gas. The nitrobenzene functions both as solvent and oxidant.

Moreover due to a relative lack of highly reactive oxygen in the process, the product formed is not the highly oxidized diphenoquinone but is rather the desired substituted biphenol.

The invention therefore comprises an effective and expeditious process of producing substituted biphenols in a single step, without the need of separating and recovering an intermediate substituted diphenoquinone product, and furthermore, without the use of a gaseous oxidizing medium such as oxygen or air.

DETAILED DESCRIPTION OF THE INVENTION

Oxidative coupling reactions of phenols are well-known reactions. In order to effect the formation of desired products it is customary to employ a substituted phenol having the positions through which carbon-to-carbon coupling is not desired blocked by protecting groups such as alkyl, aryl, cycloalkyl, halogen, alkoxy and combinations thereof having up to about 10 carbon atoms.

The substituted phenols here used are those well-known in the art as forming oxidative carbon-to-carbon coupling products. Examples are 2,6-dimethyl phenol, 2,6-diethyl phenol, 2,6-ditertiary butyl phenol, 2,6-diisobutyl phenol, 2-octyl-6-methyl phenol, 2,6-ditertiary-hexyl phenol, 2-ethyl-6-methyl phenol, 2-methyl-6-tertiary-butyl phenol, 2-cyclohexyl-6-methyl phenol, 2,6-dimethoxy phenol, 2,6-dibutoxy phenol, 2-methoxy-3-ethoxy-6-methyl phenol, 2,4-dimethyl phenol, 2,4-ditertiary-butyl phenol, 2-methyl-4-amyl phenol, 2-methyl-4-ethoxy phenol, 2-ethoxy-3,4-methyl phenol, 2,4-dimethyl-3,5-dichlorophenol, etc. Because of steric hindrance when the 2,4-substituted phenolic compounds are coupled in the ortho position, the substituent on the 3-position is preferably hydrogen, halogen or a short-chain alkyl group. Generally like phenol compounds are coupled to reduce the variety of reaction products formed, unless of course a mixture of products is acceptable. Where it is desired to dealkylate the biphenol reaction product, the preferred reaction product is substituted with tertiary butyl or other easily removable tertiary alkyl group.

The catalysts employed in the reaction are heterogeneous oxidative coupling catalysts capable of forming carbon-carbon coupled reaction products. Suitable catalysts are the noble metals such as platinum, palladium, ruthenium, rhodium, and iridium and the additional members of Group VIII and IB of the Periodic Table along with chromium, molybdenum, zinc or mixtures of the above catalysts. Preferred are noble metal-containing heterogeneous catalysts wherein the noble metal is present in a valence suitable to catalyze the carbon-to-carbon coupling of phenolic compounds under the instant process conditions. Especially preferred are platinum or palladium-containing catalysts.

Preferred are finely powdered or commutated catalysts having a large surface area in proportion to the volume of the catalyst. To attain this condition the oxidative coupling catalyst may be powdered or ground to a fine consistency or it may be deposited onto the surface of a large surface area support such as carbon, bone black, activated charcoal, alumina, clays, etc. Methods of producing such supported catalysts are well-known in the art.

As previously mentioned, the reaction employs a unique solvent, nitrobenzene, which has been found to act not only as a solvent in aiding transport and contacting of reactants, but furthermore, nitrobenzene has been found unique in acting as the oxidant according to the invented process. The nitrobenzene may be employed in any proportion. Preferably, however, it is present in about an equal molar ratio with the phenolic reactant.

The reaction is conducted at elevated temperatures of from about 30° C. to about 250° C. Generally, the hotter the reaction the faster the rate of reaction. However, excessive temperatures will lead to product decomposition. Preferred are temperatures from about 100° C. to about 200° C.

In the operation of the invention, the phenolic reactant is combined with nitrobenzene in a reactor vessel of ordinary design and construction. Glass or steel reactors may satisfactorily be employed. A catalytic amount of the heterogeneous oxidative coupling catalyst is then added. Additionally, in order to prevent isomerization of the 2,6-dihydrocarbyl phenol due to the presence of acid species from the catalyst or catalyst support, a small amount of a base such as sodium carbonate may be added. The reactor is then sealed and the mixture heated with agitation until the reaction is substantially complete.

Generally, at the preferred reaction temperatures, several hours up to about six hours are employed in the reaction.

The reaction may be conducted under an inert atmosphere if desired. However, since available oxygen is not disadvantageous to the oxidative coupling reaction, it is also suitable to operate in the presence of small amounts of oxygen as for example would be available in any air present when the reaction is begun. However, additional amounts of air or oxygen are not provided during the course of the reaction and no means for admitting gas to the reactor during the reaction need be provided.

Further suitable according to the invention is a continuous process wherein the catalyst is contained in a bed through which a stream of nitrobenzene containing the desired reactive phenolic compound is circulated.

The desired product is recovered and purified by any suitable means, for example, by crystallization upon addition of a polar solvent such as methanol.

Alternatively, where it is desired to produce a dealkylated biphenol product, a tertiary butyl-substituted biphenol may be combined with a dealkylation agent such as a strong acid, e.g., para-toluene sulfonic acid, and heated to readily produce isobutylene gas and the corresponding unsubstituted biphenol which is substantially insoluble in nitrobenzene solution. This fact aids in the expeditious recovery of the unsubstituted biphenol product.

SPECIFIC EMBODIMENTS

Having described my invention, the following examples are provided as further illustrative and are not to be construed as limiting.

EXAMPLE 1

Nitrobenzene (10 ml), 2,6-ditertiary butyl phenol (10 g) and catalyst (5 percent Pd metal on carbon, 1 g) were combined in a 50 ml glass round bottom flask, equipped with reflux condenser, temperature control, and mechanical stirrer. To determine that no oxygen was required for the reaction, the flask was purged with nitrogen. Heating and stirring were commenced and the reaction maintained at 190° C. Samples were removed periodically and analyzed by gas chromatography. Results are contained in Table I.

TABLE I

| Time (hr) | (1) Wt % of mixture | (2) Wt % of mixture | % Conversion |
|---|---|---|---|
| 0 | 45.4 | 0.3 | 0.7 |
| 1 | 28.2 | 16.5 | 36.9 |
| 2 | 20.8 | 24.3 | 53.9 |
| 3 | 12.5 | 27.7 | 68.9 |

(1)2,6-ditertiary butyl phenol
(2)2,2′,6,6′-tetratertiarybutyl-p,p′-biphenol

What is claimed is:

1. A process for producing biphenol carbon-carbon coupled condensation products of a substituted phenol of the formula:

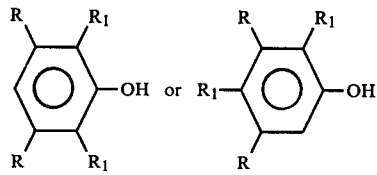

wherein each R is hydrogen, halogen, or $R_1$; and each $R_1$ is a substituent having up to 10 carbons selected from the group consisting of hydrocarbon, halohydrocarbon, and hydrocarbonoxy comprising contacting the substituted phenol at an elevated temperature with nitrobenzene under an inert atmosphere in the presence of a heterogeneous oxidative coupling catalyst capable of catalyzing the coupling reaction selected from the group consisting of platinum, palladium, ruthenium, rhodium, irridium, metals of group VII and IB of the Periodic Table, chromium, molybdenum, zinc and mixtures thereof present in a valence suitable for causing the carbon-carbon coupling of the pheolic compound.

2. A process according to claim 1 wherein the substituted phenol is 2,6-di-substituted phenol.

3. A process according to claim 1 wherein the catalyst contains platinum or palladium.

4. A process according to claim 1 wherein the temperature is between about 30° C. and about 250° C.

5. A process according to claim 2 wherein the substituted phenol is 2,6-dialkyl phenol.

6. A process according to claim 1 or 5 wherein the substituted phenol is 2,6-ditertiary butyl phenol and the product formed is 2,2′,6,6′-tetratertiary butyl-p,p′-biphenol.

7. A process according to claim 6 wherein the 2,2′,6,6′-tetratertiarybutyl-p,p′-biphenol is dealkylated by contacting with a strong acid.

8. A process according to claim 1 wherein a base is additionally present.

9. A process according to claim 8 wherein the base is sodium carbonate.

* * * * *